United States Patent [19]

Salisbury et al.

[11] Patent Number: 5,262,331
[45] Date of Patent: Nov. 16, 1993

[54] METHOD FOR MONITORING IN PEPTIDE SYNTHESIS

[76] Inventors: Stephen Salisbury, 11, Wimpole Rd., Great Eversden, Cambridge, CB3 7HR, England; John Tremeer, 32 Willow Dr., Kendal, Cumbria LA9 6AV, England; David Owen, 17, The Oaks, Milton, Cambridge CB4 4ZG, England; John Davies, 34, Granta Rd., Sawston, Cambridge CB2 4HT, England

[21] Appl. No.: 720,513
[22] PCT Filed: Aug. 27, 1990
[86] PCT No.: PCT/SE90/00549
§ 371 Date: Jun. 26, 1991
§ 102(e) Date: Jun. 26, 1991
[87] PCT Pub. No.: WO91/03485
PCT Pub. Date: Mar. 21, 1991

[30] Foreign Application Priority Data

Aug. 28, 1989 [SE] Sweden .................. 8902842

[51] Int. Cl.$^5$ .................. C07K 1/00; G01N 21/00
[52] U.S. Cl. .................. 436/86; 436/89; 436/164; 436/111; 525/54.11; 530/334; 530/337; 530/338
[58] Field of Search .................. 436/86, 89, 164, 111; 525/54.11; 530/334, 337, 338

[56] References Cited

U.S. PATENT DOCUMENTS

| | | | |
|---|---|---|---|
| 4,746,490 | 5/1988 | Saneii | 436/89 X |
| 4,755,558 | 7/1988 | Kalbag | 525/54.11 X |
| 4,800,166 | 1/1989 | Horn et al. | 436/55 |
| 4,855,486 | 8/1989 | Kalbag | 560/158 |

OTHER PUBLICATIONS

Artherton, E. et al., "Solid Phase Peptide Synthesis using Nα-Fluorenyl-methoxycarbonylamino Acid Pentafluorophenyl Esters", Journal of the Chemical Society, Chemical Communications, pp. 165-166 (1985).
Stewart, J. M. et al., "Solid Phase Peptide Synthesis", 2d ed., Pierce Chemical Company, Ill., pp. 29-30 (1984).
Krchnak et al., Int. J. Peptide Protein Res. 32, 415-416 No. 5, (1988).
Cameron et al., J. Chem. Soc. Perkin Trans., 1, 2895-2901 (1988).
Nielsen et al., Journal of Biochemical and Biophysical Methods, 20, 69080 (1989).

Primary Examiner—James C. Housel
Assistant Examiner—Jeffrey R. Snay
Attorney, Agent, or Firm—Seidel, Gonda, Lavorgna & Monaco

[57] ABSTRACT

A method for monitoring the reaction between an activated carboxylic acid derivative and an amine, such as the formation of a peptide bond in peptide synthesis, whereby an inert anionic dye component and an inert cationic component are included in the reaction system, in small relative amounts compared to the carboxylic acid derivative. The distribution of the dye component to the cationic component, when separated from the amine component, is monitored and at a given maximum value indicates a substantially quantitative reaction.

13 Claims, 5 Drawing Sheets

METHOD FOR MONITORING IN PEPTIDE SYNTHESIS

The present invention is related to the field of peptide synthesis, especially solid phase synthesis, and more particularly to a method for monitoring the time required for attachment of each amino-acid or peptide residue during the chemical synthesis of a linear combination of amino-acid residues, joined by peptide bonds.

Peptide synthesis in general is based on the reaction between an amino acid or peptide derivative, having the N-terminal alpha amino group unprotected but the C-terminal carboxyl group rendered unreactive by appropriate derivatisation, with a second amino-acid or peptide derivative of which the N-terminal alpha amino group is protected but the C-terminal carboxyl group is activated so as to enable formation of a peptide bond between the two compounds. This reaction can be carried out in solution or with one of the reacting species, usually the amino component, attached to an insoluble matrix. Immobilisation of the growing peptide chain in this way offers considerable savings in time and labour since it facilitates separation of the products of the reaction from the remaining excess reagents and soluble by-products. At the conclusion of the synthesis the assembled peptide is liberated from the support by chemical treatment. The solid phase approach is now the method of choice when chemically synthesised peptides are required.

Solid-phase peptide synthesis generally, and specifically where the present invention can be applied, comprises the following steps.

a) Removing an N-alpha protecting group from an appropriately derivatised amino-acid attached via its carboxyl group to an immobilising matrix.

b) Adding a second amino-acid derivative itself having an N-alpha protecting group and with its carboxyl group activated in such a manner as to facilitate peptide bond formation with the exposed amino group of the previous residue attached to the matrix.

c) Repeating steps a) and b) until the desired combination, termed a peptide, is obtained.

An intrinsic feature of the solid phase technique in its present forms is that intermediate peptide products cannot be purified and freed from peptides which, for any reason, do not contain the correct sequence. The method, therefore, relies for its success upon achieving reactions, both in the deprotection step a) and acylation step b), which are effectively quantitative. Removal of the alpha amino group is in practice rapid and, when the deprotection reagent flows past the substrate, is easily driven to competion. The chain elongation reaction can be by contrast problematic: for a combination of chemical, physical, and economic reasons, which stem respectively from the reactivity, molar solubility and cost of the activated amino-acid derivatives available, forcing conditions cannot be conveniently employed. An added and important complication is that the rate, and hence the time taken to achieve effective completeness of the acylation reaction is found to vary not only with the amino-acid derivative being coupled but also and in a sometimes unpredictable way with the sequence of the immobilisied substrate peptide. This condition is thought to be due to conformational properties of the peptide chain which render the amino terminus inaccessible to reagents, and its onset can prove catastrophic if the reaction conditions are not adjusted to compensate.

In solid phase synthesis, therefore, information about the progress of the acylation reaction can be of critical importance. Inefficient couplings lead to an accumulation of 'deletion' sequences such that the final product can be a complex mixture with the desired peptide only a minor component.

In the manual solid phase technique (or through operator intervention in automatic equipment) the method of choice for confirmation of total reaction involves withdrawal of a sample of the support matrix for detection of remaining amino groups (unreacted sites), usually by the use of ninhydrin (see for instance Kaiser E et al, Anal Biochem.1970 34(2) 595–8). This procedure does not readily lend itself to mechanisation and dependence on it restricts the potential of automated instrumentation. The practical approach to synthesis tends to employ reaction times which are estimates based on general experience. This means that the cycle times must be chosen long enough to cover also extreme situations which make the total synthesis time-consuming but without garantee for quantitative reactions. One innovation was the adoption of N-alpha protecting groups with measurable absorbance in the near-ultraviolet, especially the fluorenylmethoxycarbonyl (Fmoc) group (L. A. Carpino and G. Y. Han, J. Amer. Chem. Soc., 1970, 92, 5478). The total material recovered from cleavage of the protecting group can be measured spectrophotometrically and the amount is compared between successive cycles. When the amounts are similar the method provides welcome reassurance that the synthesis is proceeding satisfactorily; but if the indication is to the contrary it is too late for remedial action to be taken. The best it can offer is that, as a result of arbitrary increase in times allowed for reaction, the accumulation of deletion sequences may be prevented, or by termination of the synthesis further waste of reagents avoided.

Two approaches to achieving full feedback control of the acylation reaction have been followed with limited success in automated equipment. Both are based on the chemical properties of remaining amino groups, present after incomplete reaction. The general strategy avoids problems of dynamic range inherent in the measurement of very small changes in the overall extent of reaction. In one method, unreacted amino groups are treated, after removal of the initial acylation mixture, with a triphenylmethyl alkylating agent (Reddy MP and Voelker PJ, Int J Peptide Protein Res 31 (1988) 345–8). After washing of the synthesis support to remove excess reagent, the covalently bound portion is recovered by acidolysis and quantitated using its absorbance in the visible region of the spectrum. The second makes use of the basicity of the exposed amino groups in combination with the change of the electronic spectrum associated with ionisation of hydroxybenzotriazinone (DhbtOH) (GB8602586). This compound is one of a class of acidic catalysts for peptide synthesis which generally give access to high coupling yields without promoting significant racemisation of activated amino-acid derivatives (W. Konig and R. Geiger, Chem. Ber., 1970, 103, 2024–33). The important property in the context of monitoring is that the DhbtOH, itself colourless, protonates the unreacted amino groups and the yellow conjugate base remains bound to the support matrix. Direct spectrophotometric measurement of the synthesis support can then be used to indicate completeness of the reaction: when no amino groups remain, the colour is discharged. A closely related method employs added Bromophenol Blue as an acid-base indicator to detect unreacted amino groups (V. Krchnak and J. Wagner Collect. Czech. Chem. Commun., 1988, 53, 2542-8).

The effectiveness in practice of these methods is restricted by technical difficulties. In the first method, amino groups unreactive under one set of conditions, are probed by a second reagent. To be properly effective the reactivity in the second case must greatly exceed that of the first and, since the reduced reactivity of the amino-terminus is thought to have a steric basis, bulky tritylating reagents can be considered less than ideal. Added to this disadvantage are the additional steps required in the synthetic cycle with the associated increase in the time taken for each amino-acid addition, and the possibility that nucleophilic side-chains of residues in the growing peptide may become alkylated on repeated treatment with relatively large amounts of tritylating agent or similarly acid-labile protecting groups removed as a result of succesive acid treatments.

The use of DhbtOH as an acid - base indicator effectively avoids the problems of reactivity and steric hindrance, and the need for extra operations in the synthetic cycle since the indicator is supplied as a component of the reaction mixture. Optical measurement through the solid matrix is, however, cumbersome with absolute absorbance values depending on the individual sample of support, the peptide attached to it, and the residue being coupled. For these reasons only the rate of change of absorbance is interpretable; but this makes it difficult to distinguish intrinsically slow reactions from those slowing down as they near completion, while exhaustion of reagent before complete reaction is obtained can be misinterpreted. The technique is effective in giving advance warning when problems are encountered during a synthesis, but the data is not informative enough to enable the feedback control required in fully automated peptide synthesis instrumentation. Bromophenol Blue has been used as an alternative indicator, but it is slowly rendered colourless by acylation during extended reactions.

Fully automated peptide synthesis can be realised using the present invention which, in contrast to current methods, enables the coupling reaction to be monitored over several hours even in the case of very sluggish acylations.

Figure 1:
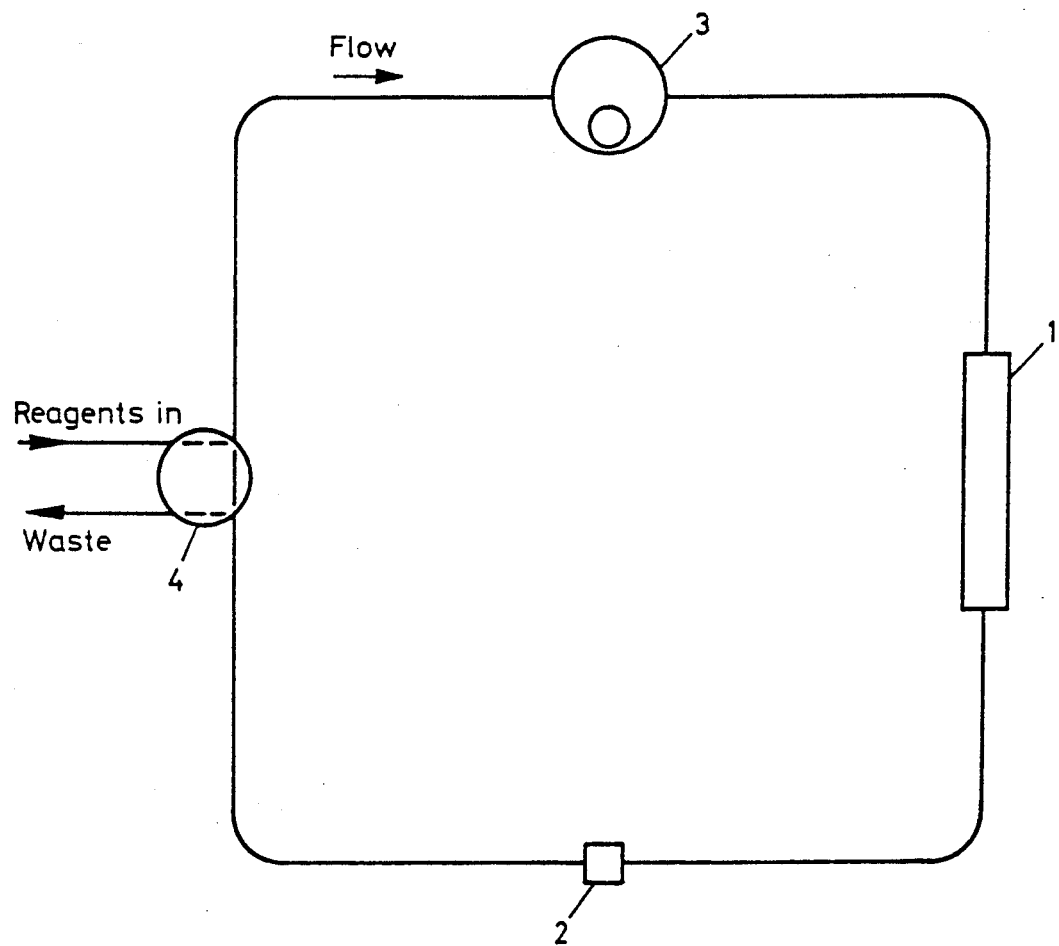
FIG. 1 is a schematic of a recirculating peptide synthesizer which may be used in the practice of the invention.

The present invention provides a means of monitoring the synthesis of linear combination of amino-acid residues by an optical, e.g. photometric method. This is attained by the method according to the invention in that amino-acid derivatives having an N-alpha amino protecting group, for instance Fmoc-amino-acid derivatives, are used in the synthesis; in that the reaction system contains an anionic substance of distinctive spectroscopic charateristics i.e. a dye; and in that the system also contains a cationic species which is substantially inert under the conditions of the acylation reaction and which is physically separable from the synthesis medium in which the peptide chain extension reaction takes place. At equilibrium the dye is distributed between all cationic species according to their relative proportions and affinities for the dye. At the beginning of the acylation reaction, protonated amino groups on the synthesis support constitute the great majority of cationic sites and will bind the anionic dye with high efficiency. As the acylation proceeds the proportion they represent of the total cations will reduce, and the progress of the reaction can be deduced from the consequent redistribution in favour of the other, inert cationic components of the system. The amount of the dye and added cationic species can be very small in molar terms compared to that of the peptide being synthesised so that the method is capable of considerable sensitivity, with a dramatic change in absorbance as the reaction approaches the end point. Typical values in a case where the dye has equal affinity for the protonated amino groups of the the growing peptide chain and for the other cation, as might be the case for another but unacylatable amine of similar pK, could be: the amout of peptide $-10^{-1}$ mol, dye $-10^{-7}$ mol, and the cation $-10^{-6}$ mol, respectively. These figures should be considered only as a guidance for using the present method but without in any way limiting the scope of the invention.

The monitoring method is based on measurement of the absorbance of the unreactive cationic species with bound dye and there is accordingly a dramatic change in this absorbance when the reaction approaches the end point.

This monitoring method can, which is obvious to those of skill in the art be used in various systems for peptide synthesis and it is not limited to any specific method for synthesis.

One object of the invention is to provide an improved method for solid phase peptide synthesis where the N-alpha protected carboxyl terminal amino-acid is chemically attached to an insoluble matrix through its carboxyl group. The synthesis proceeds via the following steps:

a) removing the N-alpha protecting group to obtain an N-alpha amino group.

b) adding an amino-acid residue, having an N-alpha protecting group and with its carboxyl group activated in such a way, either in situ or before introduction into the system, so that peptide bond formation can take place c) repeating steps a) and b) until said peptide has been obtained.

A quantity of an anionic dye is included in the reaction mixture of step b) together with a soluble cation, for instance from a suitable salt. The dye component can be chosen inter alia from Direct Yellow 29, Direct Yellow 50, Chrysophenine, Acid Yellow 38, Patent Blue VF, Patent Blue A, Quinoline Yellow, water soluble, Erioglaucine, Sulphorhodamine B, and Acid Violet 1, just to mention a few. The counter ion could be for instance diisopropylethylammonium. The reagent mixture is caused to pass continuously past the insoluble matrix upon which the peptide substrate is supported. The progress of the reaction is followed by measuring the optical density of the reagent solution. The amount of dye as well as the amount of the inert cationic species should as stated above be small in comparision with the amount of growing peptide chains with a preferred molar ratio in the range of from $10^{-4}:1$ to $10^{-8}:1$, respectively.

In a second aspect the invention provides for monitoring the peptide bond-forming reaction in peptide synthesis in the system described in the first aspect, above, using an apparatus comprised of a pump and a flow system for circulation of the reactant solution through a vessel or column containing the immobilised substrate and a spectrometric flowcell containing a second matrix, derivatised with the inert cationic species. The extent of reaction in this case is followed by measurement of the optical density of the contents of the flowcell. The immobilised cation in the flowcell serves to concentrate the dye as compared to that in the bulk solution thereby increasing the sensitivity of the method. An adquate supply of cationic species in the reciruclating solution promotes equilibration of the dye between the synthesis and monitoring phases. The matrix can be chosen among the great number of products developed for chromatography, which also have suitable optic properties. Among the preferred matrixes can be mentioned porous glass beads and silica particles. The cationic species which are immobilized on the matrix as ion exchange ligands could for instance be dimethylaminopropyl.

In a third aspect the invention is applied to solution phase peptide synthesis in which an amino-acid or peptide derivative having the N-alpha terminal alpha amino group unprotected but with the C-terminal carboxyl group rendered unreactive by appropriate derivatisation, or simply an amine, is caused to react with a second amino-acid or peptide derivative of which the C-carboxyl group is activated so as to enable formation of a peptide bond between the two compounds. This reaction mixture, according to the invention, is allowed to equilibrate with a relatively small amount, expressed in molar terms, of the immobilised cationic substance described in the second aspect above and contained within a spectrophotometric cell, and an amount of the dye. As the reaction proceeds the absorbance rises as the reactive amino groups in solution are consumed and, provided that in molar terms the amount of dye does not exceed that of the immobilised cation and that the carboxyl component of the reaction mixture is in excess, the absorbance increases to a predictable maximum value when the reaction is complete.

The method is further defined in the claims which are hereby incorporated.

The following examples illustrate the three pricipal applications of the present invention but without limiting the scope of the invention in any.

Solid-phase syntheses (Examples 1,2) were carried out according to the Fmoc-polyamide method, where the N-alpha amino group of the reagent amino-acid derivative is protected with the 9-fluorenylmethoxycarbonyl group as urethane. Syntheses were carried out in a recirculating peptide synthesier, Pharmacia LKB model 4170 and 4175 respectively, shown schematically in FIG. 1. The synthesiser has as the main components a reaction column (1) and a monitoring cell (2). The flow through the system is created with a pump (3) and a switching valve (4) is used for introducing reagents into the system and for directing the flow to waste. Carboxyl activation was by means of preformed esters of pentafluorophenol or, in the cases of Ser(But) and Thr(But), of N-hydroxybenzo-1,2,3-triazine-4-(3H)-one. Potentially reactive sidechains of the amino-acids were protected with acid-labile groups, specifically as the following derivatives: Arg(Pmc), Asp-(OBut), His(Trt), Tyr(But).

In each synthesis the carboxyl terminal amino-acid, attached via the acid-labile linkage

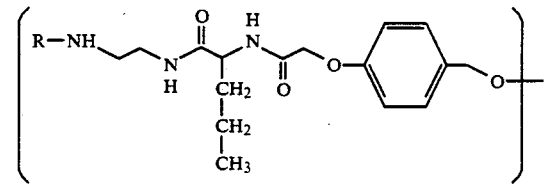

was extended in a stepwise manner to obtain the desired sequence of amino-acids. At each cycle the N-alpha protecting group of the matrix-bound, growing peptide chain (0.1 mmol) was removed by passing a mixture of piperidine and DMF (1:4 v/v) over the support. After washing with DMF, a solution containing the activated amino-acid (0.5 mmol), N-hydroxybenzotriazole (0.5 mmol), anionic dye ($10-7$ mol), and N,N-diisopropylethylamine ($2\times10^{-6}$ mol) were introduced into the recirculating system. Recirculation was maintained until the monitor output had stabilised within predetermined limits.

Suitable reporter dyes include: Direct Yellow 29; Direct Yellow 50; Chrysophenine; Acid Yellow 38; Patent Blue VF; Patent Blue A; Quinoline Yellow, water soluble; Erioglaucine; Sulphorhodamine B; Acid Violet 17.

When the assembly was complete the terminal N-alpha protecting group was removed, and cleavage from the support and deprotection effected by acidolysis with trifluoroacetic acid-water (95:5 v/v).

Dimethylaminoethyl controlled pore glass for the spectrophotometric monitoring cell was prepared by reductive methylation of commercially available aminopropyl glass spheres using formaldehyde and sodium cyanoborohydride.

EXAMPLE 1

Target: Acyl carrier protein, residues 65-74:

H-Val-Gln-Ala-Ala-Ile-Asp-Tyr-Ile-Asn-Gly-OH

Monitoring medium: Solution absorbance at 493 nm.
Reporter dye: Quinoline Yellow - water soluble

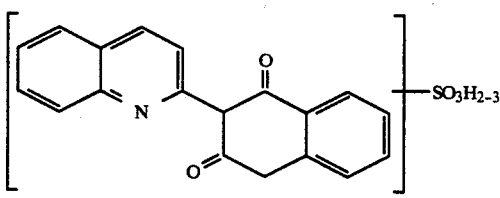

Figure 2A:
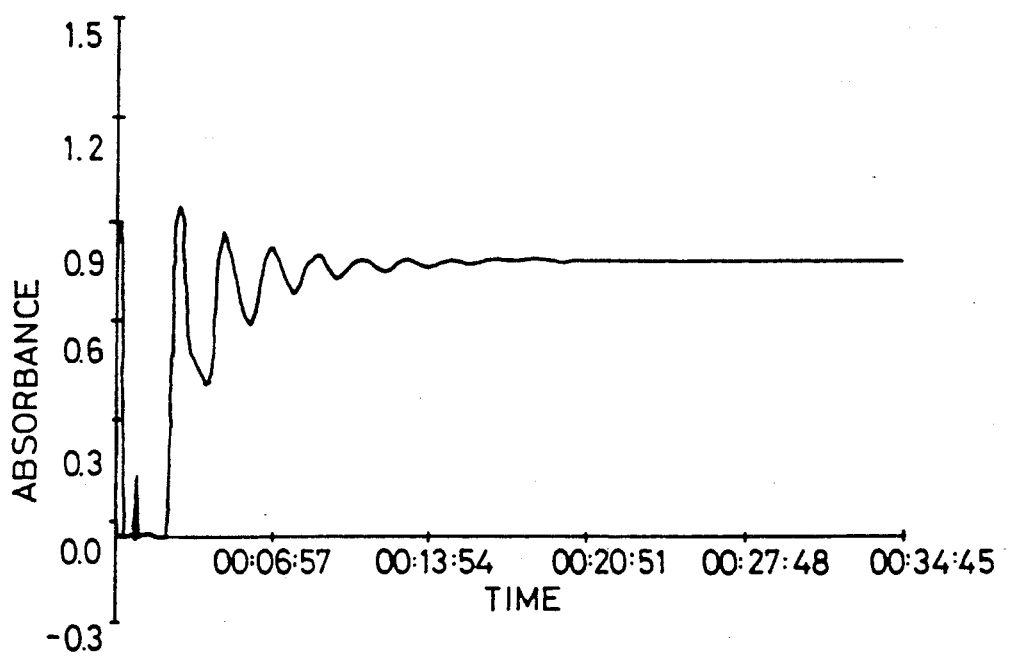
FIG. 2a is a spectrophotometric trace of the coupling of the Ala4 residue in the peptide synthesis of Example 1.
Figure 2B:
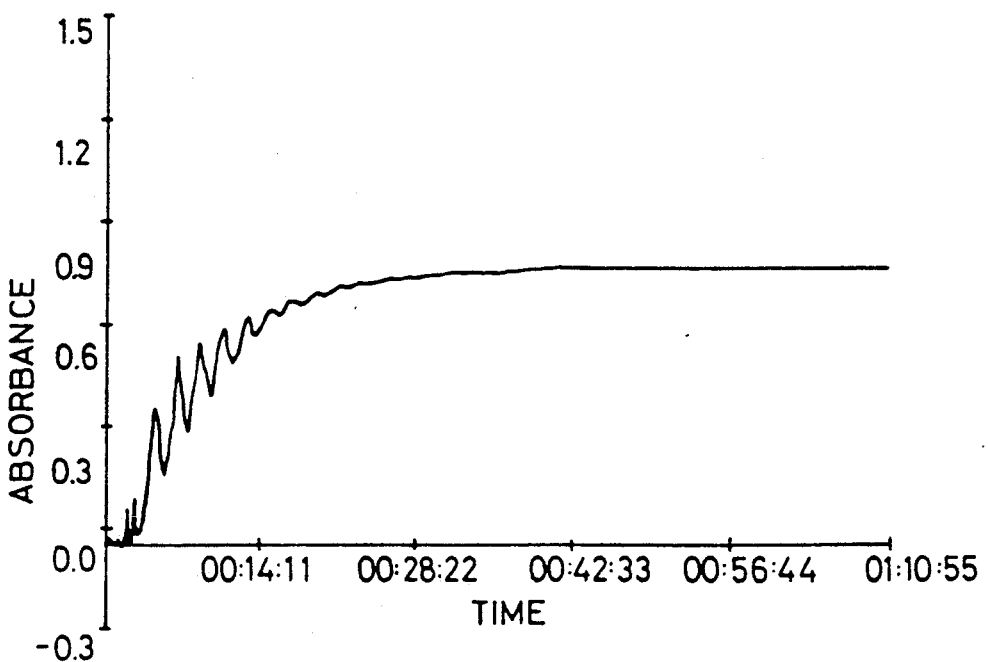
FIG. 2b is a spectrophotometric trace of the coupling of the Ile5 residue in the peptide synthesis of Example 1.
Figure 2C:
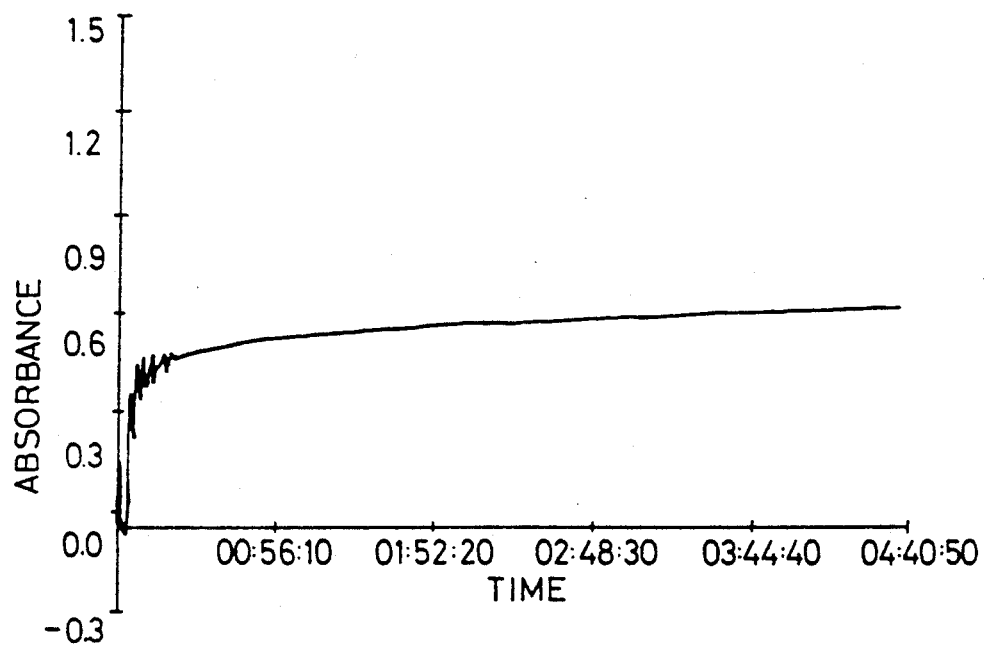
FIG. 2c is a spectrophotometric trace of the coupling of the Ala5 residue in a second acylation in the peptide synthesis of Example 1.
Figure 2D:
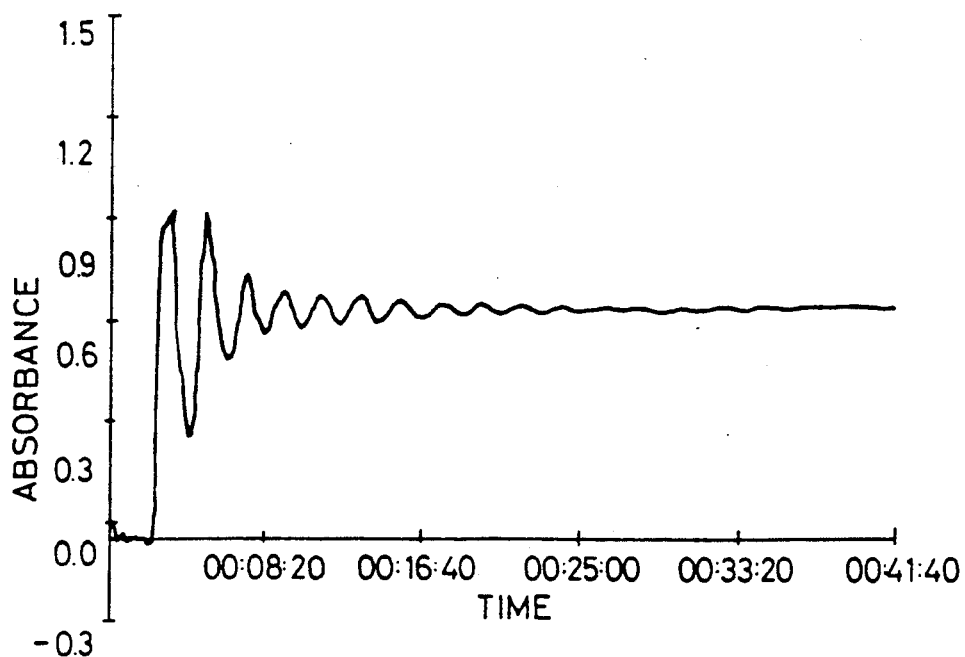
FIG. 2d is a spectrophotometric trace of the coupling of the Ile5 residue in a second acylation in the peptide synthesis of Example 1.
Figure 3:
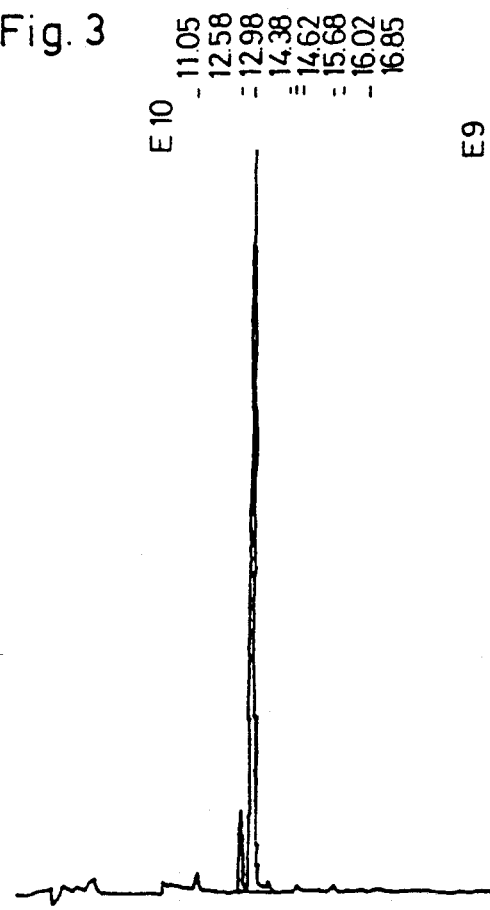
FIG. 3 is a chromatogram for the total deprotected product of Example 1, H-Val-Gln-Ala-Ala-Ile-Asp-Tyr-Ile-Asn-Gly-OH

Time required for effectively complete reaction is readily determined for rapid and slower couplings alike of which Ala4 and Ile5 (FIG. 2a,b) are typical. The notoriously sluggish reaction with activated valine can be followed over several hours and a second acylation performed to ensure full reaction (FIG. 2c,d). A chromatogram of the deprotected product is shown in FIG. 3.

EXAMPLE 2

Target: Angiotensin II

H-Asp-Arg-Val-Tyr-Ile-His-Pro-Phe-OH

Monitoring medium: Tertiary amino glass beads at 625 nm.
Reporter dye: Patent Blue VF

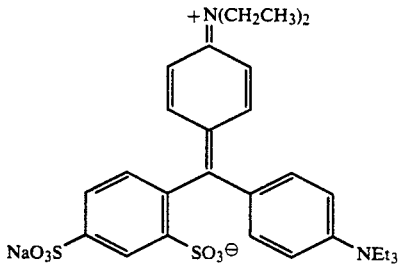

Figure 4:
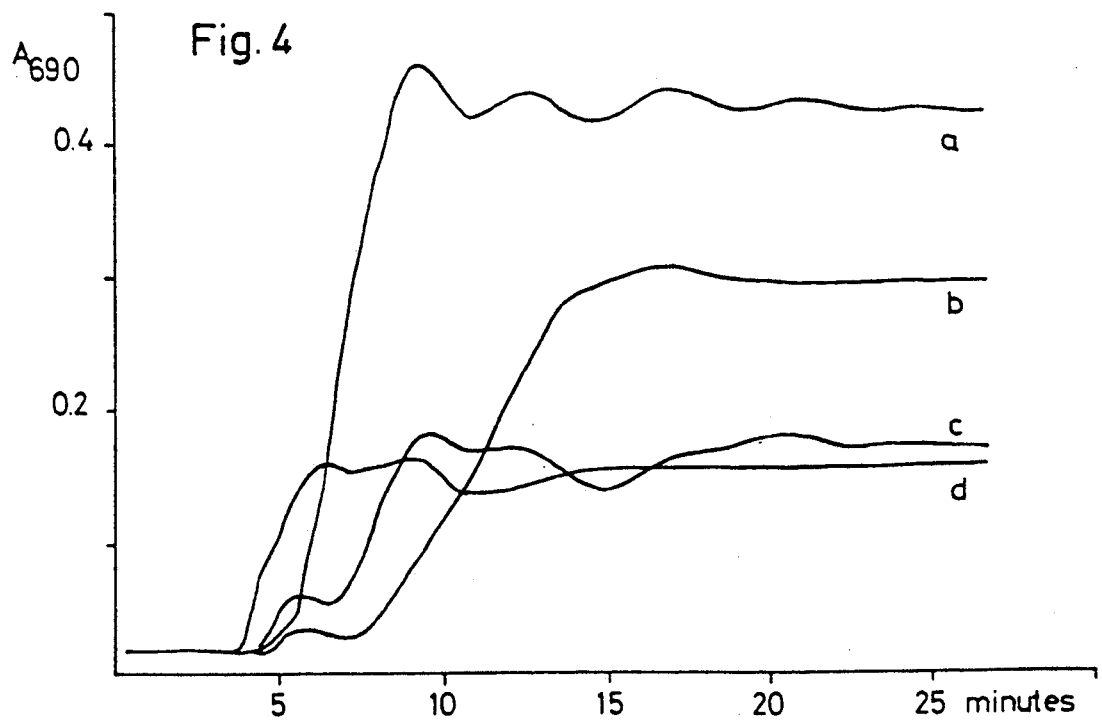
FIG. 4 is a series of spectrophotometric traces showing the coupling of the following residues in the synthesis of angiotensin II, according to Example 2: a, Pro; b, Ile; L-Arg(Pmc)Pfp, c; and Fmoc-L-His(Trt)OPfp, d.

Times to complete reaction are evident from the monitor output as before. Coupling of Pro and Ile are typical and are shown respectively in FIG. 4a,b. Progress of the reaction of Fmoc-L-Arg(Pmc)OPfp and Fmoc-L-His(Trt)OPfp (FIG. 4c,d) can also be followed: the low ultimate absorbance is characteristic of these basic amino acids in this monitoring mode.

Figure 5:
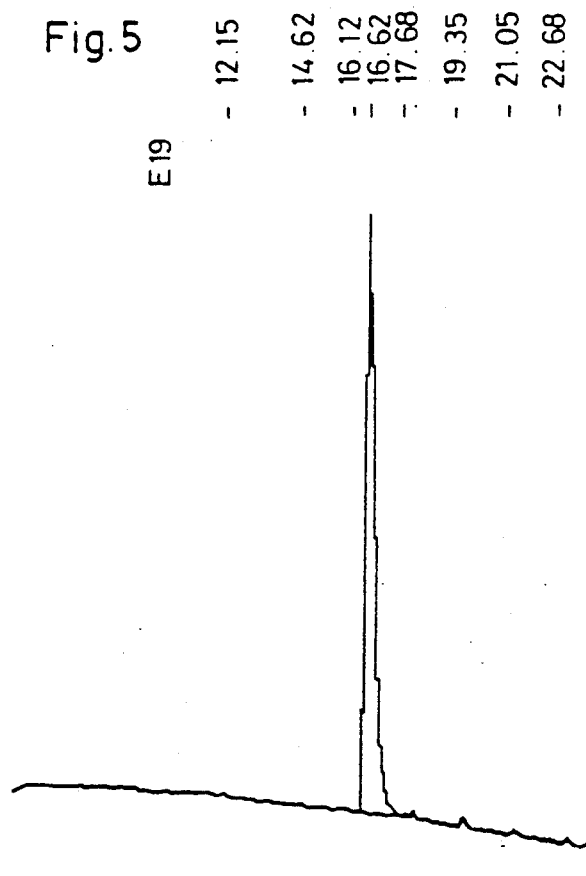
FIG. 5 is a chromatogram for the total deprotected product of Example 2, angiotensin II.

A chromatogram for the total deprotected product is shown in FIG. 5.

EXAMPLE 3

Preparation of Fmoc-L-Phe-NHCH$_2$Ph.

Figure 6:
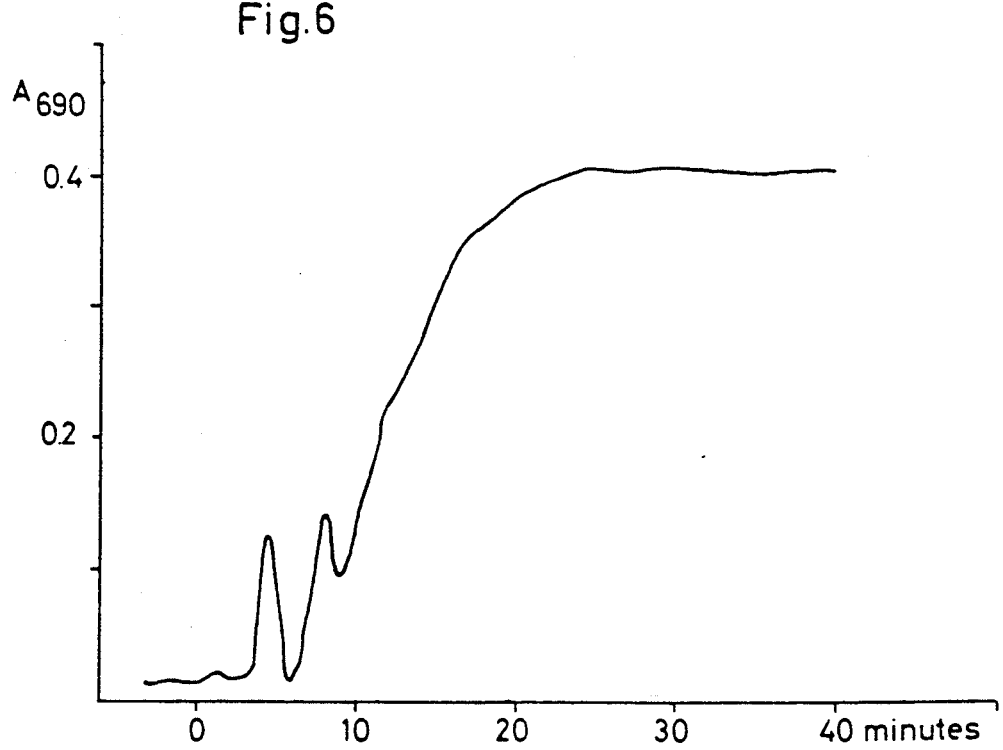
FIG. 6 is a spectrophotometric trace of the coupling of Fmoc-L-PheOPfp in the peptide synthesis of Example 3.

A DMF solution (1 ml) containing benzylamine (10.9 μL; 10-4 mol), N-hydroxybenzotriazole (0.15 g; $1.1 \times 10^{-4}$ mol) and Patent Blue VF (5) was introduced into the recirculating system (total volume 13 ml) of a Pharmacia LKB 4175 peptide synthesiser containing DMF (FIG. 1). The reaction column was filled with inert polyamide-kieselguhr synthesis support to aid mixing of the circulating liquid, and the spectrometric flow-cell was of the derivatised glass type used in Example 2. Recirculation was maintained until the monitor output was steady whereupon Fmoc-L-PheOPfp in DMF (0.066 g; 0.12 mol in 1 ml) was introduced into the system. The spectrophotometer output at 690 nm is shown in FIG. 6. A control experiment where DMF (1 ml) alone was added produced no measurable change in spectrophotometer reading resulting from the dilution.

We claim:

1. A method for monitoring in a reaction system the synthesis of a plurality of linear combinations of amino acid residues linked via peptide bonds, which synthesis starts with a plurality of amino acid residues, each of which has been protected with an N-alpha amino protecting group and rendered unreactive by appropriate derivatizing of the C-terminal carboxylic acid group thereof, said synthesis including the reaction steps of:

(a) removing the N-alpha amino protecting group from the amino acid residues to obtain alpha amino groups, (b) forming peptide bonds by reacting each said alpha amino group with an amino acid derivative which has had its N-alpha amino group protected and its carboxylic acid group activated either in situ or before its introduction into the reaction system, and (c) repeating steps (a) and (b) until the desired linear combinations of amino acid residues have been obtained, the monitoring method comprising (i) monitoring of the progress of reaction step (b) by adding to the reaction system an inert anionic dye component and an inert cationic component, which dye component has the ability to bind to the alpha amino groups obtained from reaction step (a) as well as to the added cationic component, but which dye component does not bind to the peptide bonds which are formed in reaction step (b), wherein the molar amount of the alpha amino groups which are present at the start of reaction step (b) is higher than the molar amount of the added dye component and the molar amount of the added cationic component, so that at the start of reaction step (b) most of the dye component is bound to the amino groups obtained in step (a), while at the end of reaction step (b), the dye component is essentially bound to the cationic component, and (ii) monitoring the amount of the dye component which is bound to the cationic component, relative to the amount of the dye component which is bound to amino groups from step (a), whereby a maximum value of the dye component bound to the cationic component indicates a substantially quantitative conversion of the amino groups obtained from step (a) into corresponding peptide bonds.

2. A method according to claim 1, wherein the synthesis is carried out on a solid phase which is retained in a flow cell through which a reagent solution of synthesis step (b) is pumped.

3. A method according to claim 1, wherein per mole of alpha amino group present at the beginning of reaction step (b) there are added $10^{-8}$ mols to $10^{-4}$ mols of the inert anionic dye component and $10^{-8}$ mols to $10^{-4}$ mols of the inert cationic component.

4. A method according to claim 3, wherein
    in synthesis step (b) the amino acid derivatives are present in excess of the alpha amino groups which are obtained from reaction step (a), and the molar amount of the inert anionic dye component does not exceed the molar amount of the inert cationic component.

5. A method according to claim 1 wherein the amount of the inert anionic dye component bound to the amino groups of the growing peptide chain, relative to the amount of the inert anionic dye component bound to the inert cationic component, is monitored spectrophotometrically.

6. A method according to claim 5, wherein the synthesis is carried out on a solid phase which is retained in a flow cell through which a reagent solution of synthesis step (b) is pumped.

7. A method according to claim 5 wherein the cationic component is immobilized on an insoluble matrix and the amount of the dye component bound to said immobilized cationic component is determined by measuring the absorbance of the matrix.

8. A method according to claim 7, wherein the synthesis is carried out on a solid phase which is retained in a flow cell through which a reagent solution of synthesis step (b) is pumped.

9. A method according to claim 7, wherein the synthesis is carried out in solution.

10. A method for monitoring the peptide bond-forming reaction between an activated carboxylic acid derivative and an amine component in a peptide bond-forming reaction system, in which system the carboxylic acid derivative reacts with the amine component to form an acid amide group through which said acid derivative and amine component ar linked to each other, the monitoring method comprising (a) including in said reaction system an inert anionic dye component and an inert cationic component, which inert anionic dye component has the ability to bind to the amine component and to the inert cationic component through formation of a salt, which inert anionic dye component does not bind to the peptide bond formed during the reaction of the carboxylic acid derivative and amine component, wherein the molar amount of the amine component present at the start of the reaction is higher than the molar amount of the anionic dye component and the molar amount of the inert cationic component, so that at the start of the reaction most of the anionic dye component is bound to the amine component, while at the end of the reaction, the anionic dye component is essentially all bound to the inert cationic component, (b) monitoring the amount of the anionic dye component which is bound to said cationic component relative to the amount bound to the amine component, whereby the maximum value of the anionic dye component bound to the inert cationic component indicates a substantially quantitative conversion of the amine component to the corresponding acid amide.

11. A method according to claim 10 wherein the amine component is an alpha-amino acid residue in which the carboxylic acid group is rendered unreactive by derivatization, or the carboxylic acid group is linked via a peptide bond to the nitrogen atom of a further alpha amino acid.

12. A method according to claim 10 wherein per mole of amine component at the start of the reaction there are added $10^{-8}$ mols to $10^{-4}$ mols of the inert anionic dye component and $10^{-8}$ mols to $10^{-4}$ mols of the inert cationic component.

13. A method according to claim 12 wherein the molar amount of the activated carboxylic acid derivative is in excess of the molar amount of the amine component, and wherein the molar amount of the inert anionic dye component does not exceed the molar amount of the inert cationic component.

* * * * *